United States Patent [19]

Diamond et al.

[11] 4,356,311
[45] Oct. 26, 1982

[54] PRODUCING EPOXIDE FROM OLEFIN USING METAL NITRO COMPLEXES

[75] Inventors: Steven E. Diamond, New Providence; Frank Mares, Whippany; Deborah A. Muccigrosso, Somerville; Jeffrey P. Solar, Flanders, all of N.J.

[73] Assignee: Allied Corporation, Morris Township, Morris County, N.J.

[21] Appl. No.: 332,782

[22] Filed: Dec. 21, 1981

[51] Int. Cl.³ .................................................. C07D 301/03
[52] U.S. Cl. .................................................... 549/524
[58] Field of Search ...................................... 549/524

[56] References Cited

U.S. PATENT DOCUMENTS

| | | | |
|---|---|---|---|
| 3,436,409 | 4/1969 | Hill | 260/348.24 |
| 3,641,067 | 2/1972 | Kruse | 260/348.24 |
| 3,935,272 | 1/1976 | Chapurlat | 260/348.24 |
| 4,021,453 | 5/1977 | Brill | 260/348.24 |
| 4,146,545 | 3/1979 | Leonard | 260/348.24 |
| 4,290,959 | 9/1981 | Barker | 260/348.24 |

*Primary Examiner*—Norma S. Milestone
*Attorney, Agent, or Firm*—Alan M. Doernberg; Gerhard H. Fuchs

[57] ABSTRACT

An olefinically unsaturated substrate is reacted with a transition metal nitro complex, having the transition metal bonded to the nitrogen of the nitro radical, in the presence of a thallium(III) compound as cocatalyst to cause the production of oxirane products, rather than aldehydes or ketones. The process is applicable to the production of ethylene oxide, propylene oxide, epichlorohydrin, epoxidized fatty acids and oxiranes from various other internal and terminal olefins.

10 Claims, No Drawings

PRODUCING EPOXIDE FROM OLEFIN USING METAL NITRO COMPLEXES

BACKGROUND OF THE INVENTION

The present invention relates to the production of epoxide (also called oxirane) compounds and especially to the production of epoxide compounds from olefinically unsaturated substrates by reaction with a transition metal nitro complex.

Epoxides, and other compounds having an oxirane ring such as ethylene oxide, propylene oxide, epoxidized fatty acids and the like, are conventionally produced by indirect means from the corresponding monoolefinically saturated compounds. For example, oxirane compounds are prepared by reaction of an olefin with chlorine in alkaline medium (forming e.g. epichlorohydrin) followed by reaction with base; reaction of an olefin with an organic hydroperoxide employing a Group V, VI or VII metal catalyst; reaction of an olefin with a peracid (e.g. peracetic or perbenzoic acid); and reaction of an olefin with hydrogen peroxide in the presence of arsonated polystyrene.

It has previously been disclosed in U.S. Pat. No. 4,191,696 to Tovrog et al. that transition metal nitro complexes react with a variety of oxidizable substrates to form an oxidized substrate and a metal nitroso compound, which metal nitroso compound can be oxidized with molecular oxygen back to the metal nitro compound. In that patent, when olefins are the substrate, a palladium compound is also used to complex with the olefinic group, permitting its reaction with the nitro complex to produce a carbonyl compound, which, in the case of ethylene, is acetaldehyde, and, in the case of propylene, is acetone.

It would be desirable to be able to produce oxirane compounds using molecular oxygen as the oxygen source. It is not readily apparent, however, from the above Tovrog et al. patent that metal nitro complexes are suitable intermediates or catalyst for the production of epoxides.

BRIEF DESCRIPTION OF THE INVENTION

It has been discovered that thallium(III) compounds activate olefins such that they react with transition metal nitro complexes so as to form epoxides or oxirane compounds rather than carbonyl compounds. Thus the present invention includes a process of producing an oxirane compound which comprises reacting in the liquid phase a transition metal nitro complex, having the transition metal bonded to the nitrogen atom of the nitro radical, with an olefinically unsaturated substrate free of easily oxidizable groups, in the presence of a thallium(III) compound. The by-product of this reaction is a transition metal nitroso complex, which can be isolated and reacted with molecular oxygen to regenerate the transition metal nitro complex. The above-mentioned thallium(III) compound is not reduced and remains, by in large, unchanged. It is also contemplated that, with an appropriate solvent and appropriate ligands, the transition metal nitroso complex can be oxidized in situ to reform the transition metal nitro complex, thus enabling the transition metal nitro complex to act as a catalyst, and the thallium(III) to act as a cocatalyst.

DETAILED DESCRIPTION OF THE INVENTION

The reactant or catalyst of the present invention is a transition metal nitro complex. Preferred such compounds are the nitro complexes of Group VIII metals, such as cobalt. In such complexes, the transition metal is bonded to the nitrogen atom of the nitro radical. Any transition metal which forms such a nitro complex (rather than the oxygen-bound nitrito complex) may be used. Preferred metals are the Group VIII metals such as cobalt. The transition metal nitro is made soluble by the use of appropriate ligands. In the case of Group VIII metals, there are normally four or five additional ligands besides the nitro ligand attached to the transition metal compound, which may be a combination of four monodentate ligands, two bidentate ligands, one tetradentate ligand or the like. Thus suitable ligands include 2,2'-bipyridine (a bidentate ligand), acetonitrile (a monodentate ligand) other nitriles of mono or dicarboxylic acids (mono and bidentate ligands, respectively), pyridine, pyridine-2-carboxylic acid, dimethyldithiocarbamate, dimethylglyoxime, acetylacetonate, pyridine2,6-dicarboxylic acid (a tridentate ligand), Schiff bases and porphyrins (tetradentate ligands generally) such as N,N'-bis(salicylidene)-o-phenylenediamino, N,N'-bis(salicylidene)-1,2-ethylenediamino and tetra phenylporphyrin. Particularly preferred complexes include (pyridine) (N,N'-bis-(salicylidene)-o-phenylene-diamino)nitrocobalt(III) [pyCo(saloph)NO$_2$], (pyridine)(tetraphenylporphyrin)-nitrocobalt(III) [pyCo(TPP)NO$_2$] and (tetraphenylporphyrin)nitrorhodium(III) [Rh(TPP)NO$_2$].

The olefin activator used in the process of the present invention is a thallium(III) compound, which may be organic or inorganic. Preferred inorganic thallium(III) compounds include the phosphate, sulfate, nitrate and halides. Preferred organic thallium(III) compounds include thallium(III) phenoxide, thallium(III) perfluorophenoxide and other suitable aryloxides, as well as organic thallium carboxylates such as the acetate, formate, trifluoroacetate and the like. A particular preferred thallium compound is thallium(III) benzoate.

The substrate used in the present invention may be any olefinically unsaturated substrate free of oxidizable groups. Thus the simple alkenes, including ethylene, propylene, butenes, pentenes, and the like up to octene, decene, octadecene, and higher may be used. Furthermore, the invention is not limited to terminal olefins (or alpha-olefins), since epoxides may also be formed from internal olefins such as 2-octene, 3-hexene, 5-decene and 3-hexadecene; cyclic olefins such as cyclopentene, cyclohexene, cycloheptene and cyclooctene; and substituted forms thereof such as 1-methylcyclohexene, 1-propylcyclopentene, 1,2-diethylcyclohexene and 1,2-dimethylcyclopentene. Suitable substrates can be indicated by the formula

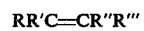

Alkenes of such formula may have any of R through R''' being hydrogen or alkyl. Thus suitable hydrocarbon substrates include isobutene, 2-methyl-2-butene, 3-methyl-2-hexene, 2,3-dimethyl-2-pentene, 2-methyl-3-ethyl-2-pentene, 2-phenyl-2-butene, 2,3-diphenyl-2-butene and the like.

Of the internal olefins (i.e. R and R'' are not H), there are three possible types of reactants: unsubstituted (R' and R''' are H), monosubstituted (only one of R' and R''' and H) are disubstituted (neither R' nor R''' are H). While the disubstituted internal olefins (e.g. 2,3-dimethyl-2-butene) have in our hands produced epoxides, the unsubstituted olefins (e.g. 2-octene) have not in certain solvents produced epoxides (e.g. in chloroform, ketones were produced; in tetrahydrofuran, no reaction was observed). It is believed, however, that with proper selection of solvent, nitro complex and thallium(III) compound, that epoxides will be produced from all three types of internal olefins.

Furthermore, any of the above substituents R, R', R" and R''' may be substituted with a variety of nonoxidizable groups such as esters, ethers, halogens, nitro and nitrile (cyano). Examples include methyl 4-pentenoate, ethyl 3,5-dimethylpentenoates, methyl 3-methylbutenoates, 3-butenyl methyl ether, 3-butenyl phenyl ether, 1-chloro-3-butene, 1-fluoro-2-butene, 4,4,4-tribromo-1-butene, 5-nitro-2-pentene, 4-pentenonitrile, 3-pentenonitrile and acrylonitrile. Easily oxidized substituents, such as amino and hydroxyl, are generally not preferred on the substrate molecule, since they will interact either with the nitro of the transition metal nitro complex, or with oxygen in the case of a catalytic process. It is not intended, however, to exclude such substituents provided that one recognizes that part or all of the product will have the oxidizable group, as well as the olefin, oxidized.

One preferred group of substrates are the mono-olefins of 2–30 carbons, including especially ethylene, propylene and 1-butene. These are preferred because of the large use of the products ethylene oxide, propylene oxide and butylene oxide. A second group of preferred substrates are the unsaturated fatty acids (particularly of 12–24 carbons), either in pure forms such as oleic acid and undecanoic acid, or in mixtures of unsaturated acids such as in a variety of naturally occurring fats and oils. A final preferred substrate is allyl chloride, with the product then being epichlorohydrin.

In the reaction, the molar ratio of nitro complex to olefin to thallium compound is not particularly critical. It is preferred, however, that the thallium compound be present in a ratio of 0.1 to 10 moles thallium compound per mole of nitro complex. In general it is preferred that the substrate be present in a molar amount at least equal to the transition metal nitro complex, with stoichiometric reactions best conducted at between 1 and 50 moles of substrate per mole of transition metal nitro complex. In the case of catalytic reactions, it is contemplated that much greater amounts of substrate are present per mole of transition metal nitro complex, with ratios of 100 to 1 or more being contemplated.

The temperature and solvent used in the present invention are not critical, provided that temperature conditions and solvents are selected so as to maintain the transition metal nitro complex, the substrate and the thallium(III) compound all in the liquid phase. It is preferred, but not required, that the product oxirane or epoxide compound as well as the by-product nitroso complex are also maintained in the liquid phase by the solvent at the reaction temperature. It is contemplated, however, that either the product or the by-product could precipitate from the solution, for product recovery in the case of the oxirane compound and for isolation and reoxidation in the case of the nitroso by-product. Thus while solvents are not particularly critical, a preferred group of solvents are the aprotic solvents represented by the halogenated hydrocarbons, the ethers, tetrahydrofuran and dioxane. Especially preferred solvents include chloroform and tetrahydrofuran.

Preferred temperatures are about 10°–100° C., and preferably about 50°–70° C. The pressure is not critical, especially if the nitroso complex is not to be regenerated in situ with oxygen. If oxygen is to be used, it is preferred that it has a partial pressure of at least 50 kPa, and more preferably at least 100 kPa. Similar oxygen pressures are preferred if the nitroso complex is to be reoxidized to the nitro complex in a separate step.

The present invention is illustrated by the following examples which are intended to be non-limiting. After each example, a comparative example without nitro complex is given, confirming that the product formed cannot be attributed to reduction of the thallium(III) compound.

EXAMPLE 1

254.9 mg (0.320 mmol) of pyCo(TPP)NO$_2$ (prepared as described in U.S. Pat. No. 4,191,696), 1050.0 mg (1.85 mmol) of thallium(III) benzoate, and approximately 650 mg (5.32 mmol) of benzoic acid were added to a thick walled glass reactor tube containing a magnetic stir bar. After degassing these solids on a vacuum line for several hours, 68.9 mg (0.442 mmol) of n-undecane (a gas chromatography internal standard) was added by syringe. Tetrahydrofuran (10 mL) and 1-octene (1 mL) were then distilled into the tube. The reactor was then stirred for approximately 5 hours at 60° C. At this time the mixture was analyzed by standard gas chromatographic techniques and found to contain 21.1 mg (0.165 mmol) of octene oxide. A trace amount of 2-octanone was also present.

COMPARATIVE EXAMPLE 2

1094.1 mg (1.93 mmol) of thallium(III) benzoate and approximately 650 mg (5.32 mmol) of benzoic acid were added to a thick walled glass reactor tube containing a magnetic stir bar. After degassing these solids on a vacuum line for several hours, 70.4 mg (0.451 mmol) of n-undecane (a gas chromatography internal standard) was added by syringe. Tetrahydroforan (10 mL) and 1-octene (1 mL) were then distilled into the tube. This reactor was then stirred for approximately 5 hours at 60° C. The mixture was then analyzed by standard gas chromatographic techniques and found to contain 3.8 mg (0.030 mmol) of octene oxide. A trace amount of 2-octanone was also present.

EXAMPLE 3

Example 1 was repeated with 255.2 mg (0.321 mmol) of pyCo(TPP)NO$_2$, 1003.5 mg (1.77 mmol) of thallium-(III) benzoate, approximately 650 mg (5.32 mmol) of benzoic acid, 70.7 mg (0.453 mmol) of n-undecane, 10 mL of chloroform and 1 mL of 1-octene. After stirring for approximately 2 hours at room temperature, the reaction mixture was analyzed by standard gas chromatographic techniques and found to contain 22.5 mg (0.176 mmol) of octene oxide and 12.5 mg (0.097 mmol) of 2-octanone.

COMPARATIVE EXAMPLE 4

Comparative Example 2 was repeated with 1047.4 mg (1.85 mmol) of thallium(III) benzoate, approximately 650 mg (5.32 mmol) of benzoic acid, 70.5 mg (0.452 mmol) of n-undecane, 10 mL of chloroform and 1 mL of 1-octene. After stirring for approximately 3 hours at room temperature, the reaction mixture was analyzed by standard gas chromatographic techniques and found to contain 1.0 mg (0.010 mmol) of octene oxide and a trace amount of 2-octanone.

EXAMPLE 5

Example 1 was repeated with 252.1 mg (0.317 mmol) of pyCo(TPP)NO$_2$, 1120.0 mg (1.98 mmol) of thallium-(III) benzoate, approximately 650 mg (5.32 mmol) of benzoic acid, 74.2 mg (0.476 mmol) of n-undecane, 10 mL of tetrahydrofuran and 1 mL of propylene. After stirring this reaction mixture for approximately 3 hours at 60° C., analysis by standard gas chromatographic techniques revealed 8.1 mg (0.14 mmol) of propylene oxide and 0.5 mg (0.009 mmol) of acetone present in the reaction mixture.

COMPARATIVE EXAMPLE 6

Comparative Example 2 was repeated with 1094.5 mg (1.93 mmol) of thallium(III) benzoate, approximately 650 mg (5.32 mmol) of benzoic acid, 68.5 mg (0.439 mmol) of n-undecane, 10 mL of tetrahydrofuran, and 1 mL of propylene. After stirring for approximately 3 hours at 60° C. the reaction mixture was analyzed by standard gas chromatographic techniques and found to contain 0.6 mg (0.01 mmol) of propylene oxide and a trace amount of acetone.

EXAMPLE 7

Example 1 was repeated with 260.5 mg (0.327 mmol) of pyCo(TPP)NO$_2$, 1027.5 mg (1.81 mmol) of thallium-(III) benzoate, approximately 650 mg (5.32 mmol) of benzoic acid, 72.1 mg (0.462 mmol) of n-undecane, 10 mL of chloroform, and 1 mL of propylene. After stirring for approximately 1 hour at room temperature the reaction mixture was analyzed by standard gas chromatographic techniques and found to contain 10.0 mg (0.172 mmol) of propylene oxide and 2.7 mg (0.047 mmol) of acetone.

COMPARATIVE EXAMPLE 8

Comparative Example 2 was repeated with 1084.7 mg (1.91 mmol) of thallium(III) benzoate, approximately 650 mg (5.32 mmol) of benzoic acid, 68.4 mg (0.438 mmol) of n-undecane, 10 mL of chloroform, and 1 mL of propylene. After stirring for approximately 1 hour at room temperature the reaction mixture was analyzed by standard gas chromatographic techniques and found to contain only trace amounts of propylene oxide and acetone.

What is claimed is:

1. A process of producing an oxirane compound which comprises reacting in the liquid phase a transition metal nitro complex, having the transition metal bonded to the nitrogen atom of the nitro radical, with an olefinically unsaturated substrate free of easily oxidizable groups, in the presence of a thallium(III) compound.

2. The process of claim 1 wherein said thallium compound is a thallium(III) carboxylate.

3. The process of claim 2 said thallium compound is thallium(III) benzoate.

4. The process of claim 1 or 2 or 3 wherein said transition metal nitro complex is a Group VIII metal nitro complex.

5. The process of claim 4 wherein said Group VIII metal nitro complex is a cobalt nitro complex.

6. The process of claim 1 wherein said substrate is an alkene of 2–30 carbons.

7. The process of claim 6 wherein said alkene is ethylene.

8. The process of claim 6 wherein said alkene is propene.

9. The method of claim 1 wherein said substrate is an olefinically unsaturated fatty acid.

10. The process of claim 1 wherein said substrate is allyl chloride.

* * * * *